(12) United States Patent
Furuichi (10) Patent No.: US 8,909,324 B2
(45) Date of Patent: Dec. 9, 2014

(54) OPTICAL COHERENT TOMOGRAPHIC IMAGE FORMING APPARATUS AND CONTROL METHOD THEREOF

(75) Inventor: Junya Furuichi, Isehara (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 142 days.

(21) Appl. No.: 13/537,218

(22) Filed: Jun. 29, 2012

(65) Prior Publication Data

US 2013/0006105 A1    Jan. 3, 2013

(30) Foreign Application Priority Data

Jun. 30, 2011    (JP) ................................. 2011-146296

(51) Int. Cl.
*A61B 5/05* (2006.01)
*A61B 5/00* (2006.01)

(52) U.S. Cl.
CPC ....... *A61B 5/0066* (2013.01); *A61B 2560/0223* (2013.01); *A61B 5/0084* (2013.01)
USPC ........................................................ 600/427

(58) Field of Classification Search
CPC .............. A61B 5/0066; A61B 5/0084; A61B 2560/0223; A61B 2562/223; G02B 6/4402; G02B 6/4405
USPC ........................................................ 600/427
See application file for complete search history.

(56) References Cited

U.S. PATENT DOCUMENTS

| 7,738,941 | B2 | 6/2010 | Hirota |
| 2007/0244391 | A1 | 10/2007 | Hirota |
| 2010/0130872 | A1 | 5/2010 | Irisawa |

OTHER PUBLICATIONS

Extended European Search Report dated Nov. 5, 2012, issued by the European Patent Office in the corresponding European Application No. 12174165.6. (6 pages).

*Primary Examiner* — Sanjay Cattungal
*Assistant Examiner* — Bo J Peng
(74) *Attorney, Agent, or Firm* — Buchanan Ingersoll & Rooney PC (57) ABSTRACT

An optical coherent tomographic image forming apparatus including a light guide configured to divide a light into a measurement light and a reference light; a flush unit configured to discharge a flush liquid into a body lumen; a refractive index setting unit configured to set a refractive index of the flush liquid; an adjustment value setting unit configured to set an adjustment value; a calibration unit for adjusting the length of the reference optical path or the length of the measurement optical path based on the adjustment value; an image construction unit configured to construct a cross-sectional image; and an offset value calculation unit for calculating an offset value of the length of the reference optical path based on a changed refractive index when the refractive index of the flush liquid is changed by the refractive index setting unit after calibration is executed by the calibration unit.

21 Claims, 11 Drawing Sheets

OPTICAL COHERENT TOMOGRAPHIC IMAGE FORMING APPARATUS AND CONTROL METHOD THEREOF

CROSS REFERENCE TO RELATED APPLICATION

This application claims priority to Japanese Patent Application JP2011-146296 filed on Jun. 30, 2011, the entire content of which is hereby incorporated by reference.

BACKGROUND DISCUSSION

Medical treatments inside a blood vessel using a highly-functional catheter such as a balloon catheter, stent or the like are generally known. Whether for the diagnosis before the surgical-operation thereof or for the progress confirmation after the surgical-operation, it has become popular to use an imaging apparatus for diagnosis such as an optical coherent tomographic diagnosis (OCT: Optical Coherence Tomography) apparatus or the like.

The imaging apparatus for diagnosis includes a catheter installed with an optical fiber on the distal end of which an optical lens and an optical mirror are mounted. The imaging apparatus is configured such that the catheter is inserted inside a blood vessel of a patient, light is illuminated onto the blood vessel wall via a rotatable optical mirror, a radial scan is carried out by light-receiving the reflected light from the blood vessel via the optical mirror and thereafter, a cross-sectional image of the blood vessel is constructed based on the reflected light that is obtained. In addition, an improved type of OCT has been developed as an optical coherent tomographic diagnostic apparatus utilizing wavelength sweep (SS-OCT Apparatus: Swept-source Optical coherence Tomography Apparatus).

According to the basic principle of the optical coherent tomographic diagnostic apparatus, light outputted from a light source inside the apparatus is divided into a measurement light and a reference light, and the measurement light is emanated toward an optical mirror of an optical fiber inside the above-mentioned catheter. Then, scattered light reflected by a biological tissue is light-received via the same optical fiber, an interference light is obtained with respect to reference light reflected by way of a predetermined distance, and a tomographic image of a biological tissue (blood vessel) in the vicinity of the catheter is obtained based on the intensity of the interference light (for example, see U.S. Pat. No. 7,738,941).

However, a blood cell component such as a red blood cell or the like is present inside the blood vessel. Light reflection thus occurs on the surface of the blood cell component and hinders obtaining an aimed highly accurate tomographic image of the blood vessel. Consequently, in order to exclude the blood cell component, it is known to temporarily create a state in which no blood cell component exists by discharging liquid such as a physiological salt solution, a contrast agent or the like inside the blood vessel. Emanation of the light and light-receiving of the reflected light is then carried out while the blood vessel is in this temporary state. The operation of discharging the liquid into the blood vessel is referred to generally as a flush operation and the liquid discharged at that time is referred to as flush liquid.

For the flush liquid, there are several types provided corresponding to the use purposes thereof. Specifically, as explained previously, these are a contrast agent, a physiological salt solution, and a mixed liquid thereof in which the mixing ratio thereof is different.

A problem arises, however, that the refractive index of the light is different depending on the type of the flush liquid. As well known in the past, the light speed propagating inside a medium is dependent on the refractive index which that medium possesses. Therefore, when the apparatus is set up with a flush liquid which is different from the flush liquid actually used, a phenomenon occurs in which the obtained scale of the tomographic image of the blood vessel is different from the actual scale.

Generally, when the flush liquid to be used is determined, before the flush operation, an image of the boundary surface between the catheter and the blood is created and displayed by rotating the optical mirror inside the catheter. Then, the refractive index of the utilized flush liquid is made a parameter and while the optical path length of the reference light is adjusted, an operation is carried out (generally, referred to as calibration operation) which makes the image (having an approximately round shape) on the boundary surface thereof coincide with a circle (land mark) which becomes a preset reference. Thereafter, a flush operation is actually carried out and the optical mirror rotating inside the catheter is moved at a constant speed along the axis of the blood vessel. The movement of the rotating optical mirror corresponds also to a pull-back operation of the rotating optical fiber, so that it is generally referred to as a "pull-back operation". In addition, the series of operation for obtaining the image is called as "imaging operation".

If for some reason, after the calibration operation is carried out, the type of flush liquid being used must be changed or if the refractive index of the flush liquid, which was set when carrying out the calibration operation, has been set erroneously, naturally, it is then necessary to carry out the calibration operation again after changing the refractive index of the flush liquid to a correct one. This is because there is a possibility, in the diagnosis of a blood vessel before a surgical-operation of arranging and indwelling a stent at a blood vessel, that the diagnosis is flawed when there is an error in the scale and there could occur a situation in which a stent having an erroneous size might be determined.

Further, in a case where it is recognized that there was an error in the setting of the set flush liquid after carrying out the flush operation and the pull-back operation, the operations subsequent to the calibration operation must be carried out again and thus occurs a situation in which the surgical-operation time period and the number of surgical-operations will increase, and the stress thereof will be exerted on the patient.

SUMMARY

An optical coherent tomographic image forming apparatus comprising a light source, a light guide configured to guide a light outputted from the light source and divide the light into a measurement light and a reference light, the light guide comprising a measurement optical path and a reference optical path, an optical probe having a distal end and a proximal end, the distal end configured for insertion into a body lumen, a flush unit comprising a flush liquid container and a flush liquid discharger, the flush unit configured to discharge flush liquid into the body lumen, a refractive index setting unit configured to set a refractive index of the flush liquid, an adjustment value setting unit configured to set an adjustment value for adjusting a difference between a length of the measurement optical path and a length of the reference optical path, the adjustment value being determined using the refractive index, a calibration unit comprising an optical path length adjuster for adjusting the length of the reference optical path or the length of the measurement optical path based on the adjustment value, an image construction unit configured to construct a cross-sectional image based on a light intensity of an interference light that is obtained from a reflected light obtained by emanating the measurement light from the optical probe toward a biological tissue defining the body lumen while the flush liquid subsists in the body lumen, and an offset value calculation unit for calculating an offset value of the length of the reference optical path based on a changed refractive index when the refractive index of the flush liquid is changed by the refractive index setting unit after calibration is executed by the calibration unit.

DETAILED DESCRIPTION

An imaging apparatus for diagnosis will be described below by reference to the embodiments disclosed here as examples and in detail in accordance with the attached drawings.

Figure 1:
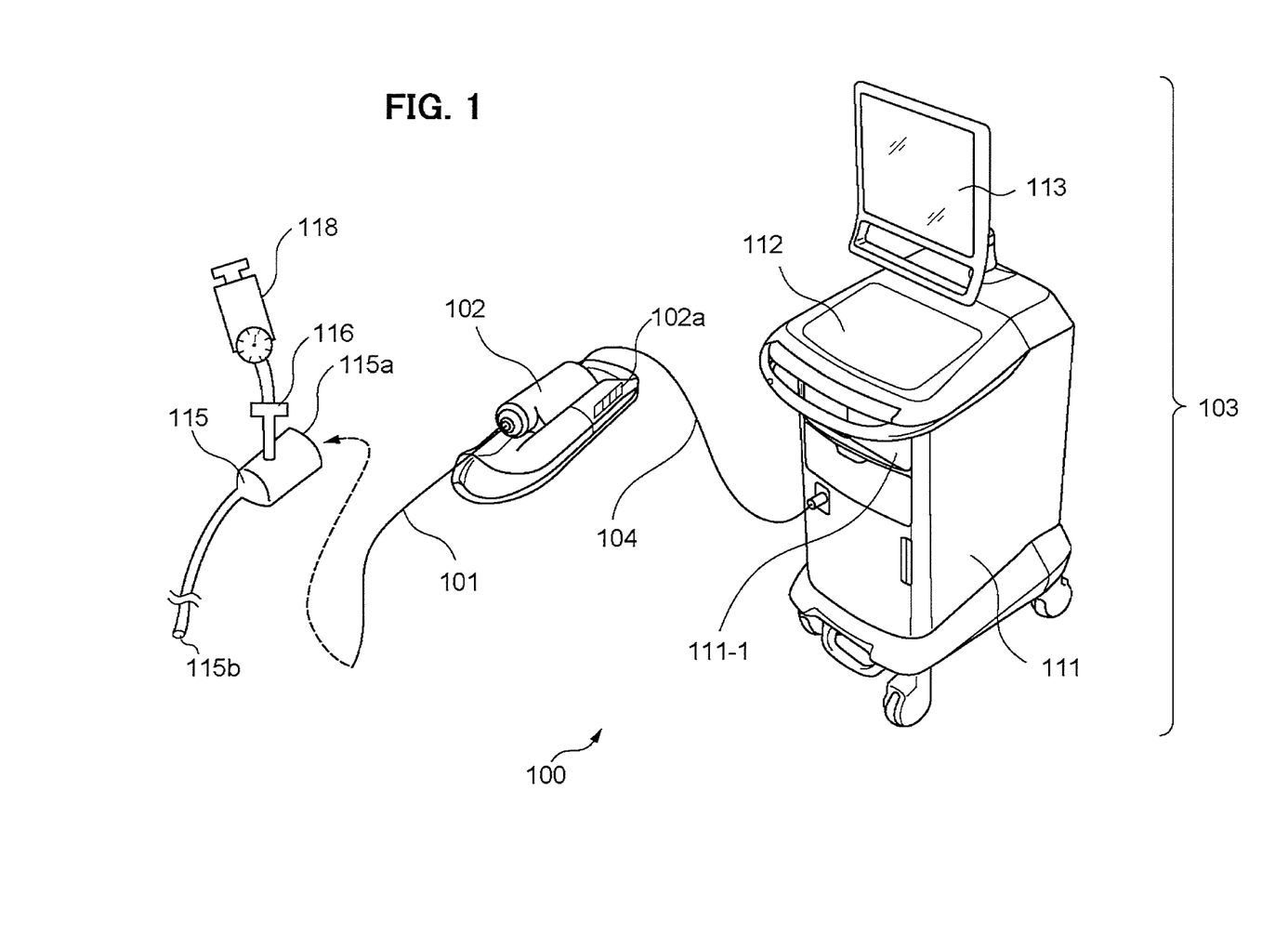
FIG. 1 is a schematic view showing the overall configuration of an imaging apparatus for diagnosis according to an embodiment disclosed here by way of example.

FIG. 1 is a view showing a system configuration and an outward-appearance of a wavelength sweep type optical coherent tomographic diagnostic apparatus (SS-OCT apparatus) according to one embodiment of the disclosure (hereinafter, referred to as imaging apparatus for diagnosis). As shown in FIG. 1, an imaging apparatus for diagnosis 100 is provided with an optical probe unit 101, a scanner and pull-back unit 102 and an operation control apparatus 103.

Further, the optical probe unit 101 is covered by a guiding catheter 115 in order to transmit flush liquid to a blood vessel region which is a diagnosis target. At a rear end 115a of the guiding catheter 115, as shown by an indicated arrow in the drawing, an insertion hole is provided for inserting the optical probe unit 101 therein and at a distal end 115b thereof, a mouth portion is provided from which the distal end portion of the optical probe unit 101 can be exposed to the outside. Further, on the guiding catheter 115, a port 116 is provided for connecting a flush liquid container 118 housing flush liquid. The flush liquid container 118 has a plunger for discharging the housed flush liquid. The plunger, the port 116 and the guiding catheter 115 thus comprise a flush discharger. The flush liquid container 118, the port 116 and the guiding catheter 115 are collectively called a "flush unit". By operating the flush unit, a situation is created in which the flush liquid housed in the inside thereof is discharged through the distal end portion 115b.

The scanner and pull-back unit 102 and the operation control apparatus 103 are connected by a signal line and optical fiber 104. The guiding catheter 115 housing the optical probe unit 101 is directly inserted inside a body lumen such as a blood vessel or the like and measures the state of a biological tissue by using an imaging core 201 provided in the optical probe unit 101. The optical probe unit 101 includes an optical fiber 236 which passes through the inside thereof and a catheter sheath 403 which covers the outside thereof, and at least the distal end portion thereof includes a transparent member (details will be mentioned later).

The scanner and pull-back unit 102 grasps a root portion 101a of the optical probe unit 101 and concurrently, by the rotation of a built-in motor thereof, the radial operation of the imaging core 201 inside the optical probe unit 101 is defined. Also, the scanner and pull-back unit 102 carries out an operation (pull-back process) for pulling back the optical fiber 236, which is rotating inside the optical probe unit 101, at a constant speed by driving another built-in motor. Performing a series of the above operation, i.e., imaging operation, makes it possible to obtain a tomographic image of a blood vessel, which is continuous along the axis of the blood vessel. Also, the scanner and pull-back, unit 102 is provided with an operation unit 102a having various kinds of instruction switches for instructing the setting of the rotation speed, the start and stop of the rotation, and the pull-back of the optical fiber 236 inside the optical probe unit 101.

For formation of an optical coherent tomographic image of biological tissue such as a blood vessel or the like, the operation control apparatus 103 includes a function for inputting various kinds of set values, and a function for processing data obtained by measurement and for displaying them as a tomographic image. In the operation control apparatus 103, the reference numeral 111 indicates a main body control unit, which processes data obtained by measurement, outputs a processed result and so on. The reference numeral 111-1 indicates a printer, which prints a processed result from the main body control unit 111. Also, although not shown, a data storage unit is also included, such as a hard disk drive and/or a DVD recorder for storing data. The reference numeral 112 indicates an operation panel and a user carries out inputting of various kinds of set values including the refractive index of flush liquid and inputting of instructions through the operation panel 112. The reference numeral 113 indicates an LCD monitor used as a display apparatus, which displays a setting screen and a tomographic image or the like which is a processed result in the main body control unit 111.

Figure 2:
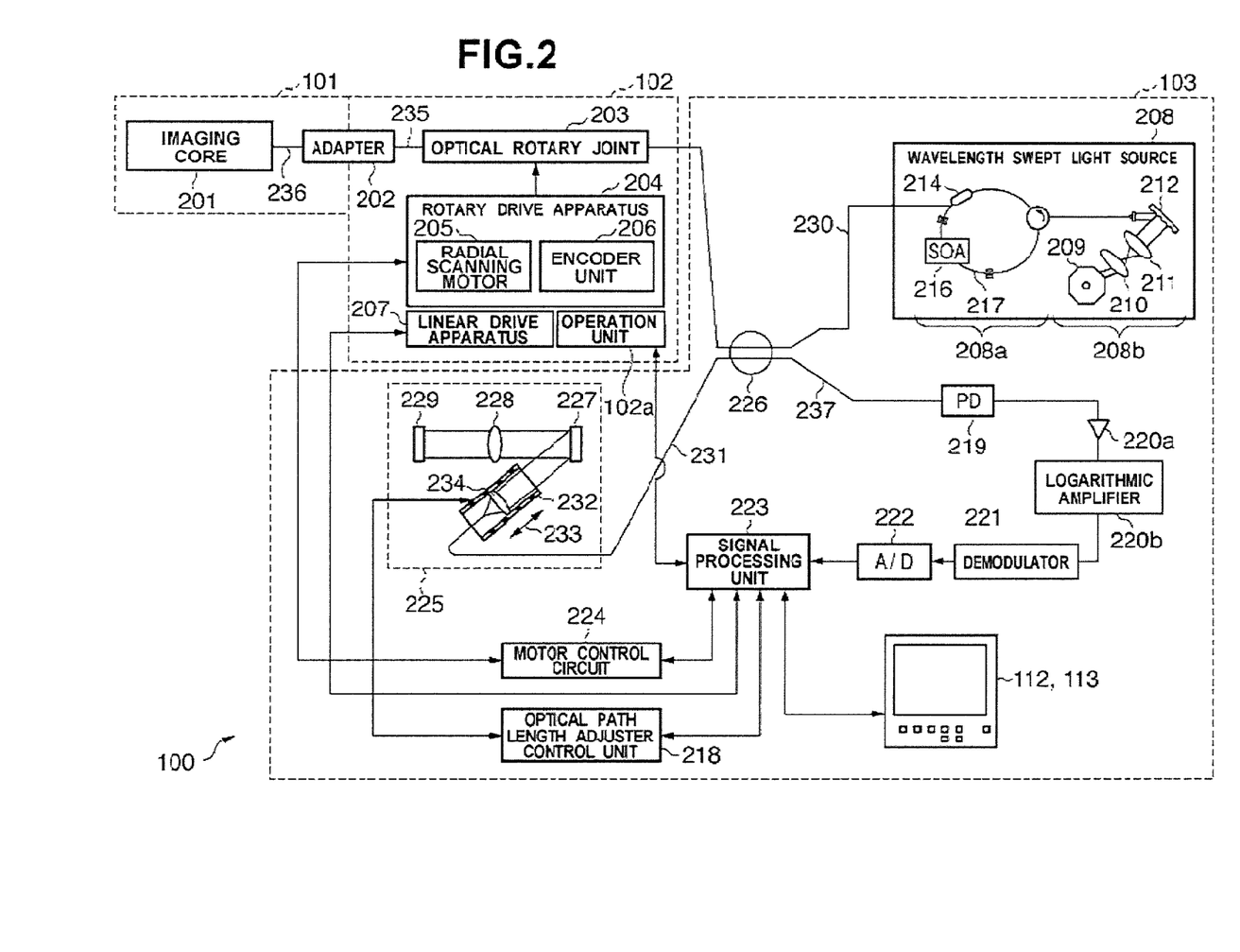
FIG. 2 is a functional block diagram showing an imaging apparatus for diagnosis.

FIG. 2 is a functional diagram of the imaging apparatus for diagnosis 100 shown in FIG. 1. In the illustrated drawing, the reference numeral 208 indicates a wavelength swept light source for which a swept laser is used. The wavelength swept light source 208 is one kind of extended-cavity laser composed of a light source unit 208a having an optical fiber 217 coupled with a SOA 216 (semiconductor optical amplifier) in a ring form and a polygon scanning filter 208b. The light outputted from the SOA 216 advances inside the optical fiber 217, enters into the polygon scanning filter 208b and the light whose wavelength is selected herein is amplified by the SOA 216 and finally outputted from a coupler 214. The polygon scanning filter 208b selects the wavelength by using a combination of a diffraction lattice 212 for light splitting and a polygon mirror 209. The light split by the diffraction lattice 212 is focused on the surface of the polygon mirror 209 by two lens (210, 211). Only the light having a wavelength that it is perpendicular to the polygon mirror 209 returns through the same optical path and is outputted from the polygon scanning filter 208b, and thus, time sweeping of the wavelength is carried out by rotating the polygon mirror 209. The polygon mirror 209 is, for example, a 72-hedron mirror and the rotation speed thereof is around 50000 rpm. A unique wavelength sweep system in which the polygon mirror 209 and the diffraction lattice 212 are combined enables wavelength sweeping at high speed and high power output.

The light from the wavelength swept light source 208 which was outputted from the coupler 214 enters one end of a first single mode fiber 230. The first single mode fiber 230 is led to a photo coupler 226 which is optically coupled with a second single mode fiber 231, and from there it is transmitted so as to be split in two. The first single mode fiber 230 and the photo coupler 226 represent an example of a light guide configured to guide light outputted from the source 208 and divide the light into a measurement light directed along a measurement optical path and a reference light directed along a reference optical path.

On the side of the first single mode fiber 230 more distal than the photo coupler unit 226, there is provided a scanner and pull-back unit 102. Inside a rotary drive apparatus 204 of the scanner and pull-back unit 102, an optical rotary joint (photo coupling unit) 203 is provided which couples a non-rotation portion (fixed portion) and a rotation portion (rotationally driven portion) and which transmits light. Further, the distal side of a fourth single mode fiber 235 inside the optical rotary joint 203 is connected with a fifth single mode fiber 236 of the optical probe unit 101 and freely detachable therefrom through an adapter 202. Thus, the light from the wavelength swept light source 208 is transmitted to the fifth single mode fiber 236 which is passed through the inside of the imaging core 201 for repeating light transmission and reception, and which is rotationally drivable.

The light transmitted to the fifth single mode fiber 236 is illuminated with respect to the biological tissue such as the blood vessel or the like from the distal end side of the imaging core 201 while being radially operated. Then, a portion of the reflected light scattered at the surface or in the inside of the biological tissue is taken-in by the imaging core 201 and returned to the first single mode fiber 230 side by way of the opposite optical path, and a portion thereof is moved to the second single mode fiber 237 side by the photo coupler unit 226. In the photo coupler unit 226, the reflected light is mixed with a reference light (mentioned later) and is light-received as an interference light by a photo detector (photo diode in the exemplified embodiment and hereinafter, referred to as PD) 219.

The rotational unit side of the optical rotary joint 203 is rotationally driven by a radial scanning motor 205 of a rotary drive apparatus 204. The rotary angle of the radial scanning motor 205 is detected by an encoder unit 206. Further, the scanner and pull-back unit 102 includes a linear drive apparatus 207 and defines the operation in the insertion direction (axis direction) of the imaging core 201 based on an instruction from a signal processing unit 223. The axial movement is realized by a mechanism in which the linear drive motor inside the linear drive apparatus 207 is operated based on the control signal from the signal processing unit 223.

A variable mechanism 225 of the optical path length is provided for fine-adjusting the optical path length of the reference light at the distal end side from the photo coupler unit 226 of the second single mode fiber 231. The variable mechanism 225 for the optical path length is provided with the optical path length changing unit for changing the optical path length which corresponds to the fluctuation of the length thereof such that the fluctuation of the length of the individual optical probe unit 101 can be absorbed such as in the case of the optical probe unit 101 being exchanged. The second single mode fiber 231 and the collimating lens 234 are provided on a one-axis stage 232 which is freely movable toward the optical axial direction thereof, as shown by arrow 233, and forms an optical path length adjuster.

More specifically, the one-axis stage 232 forms the optical path length changing unit having a sufficient range for varying the optical path length that it can absorb the fluctuation of the optical path length of the optical probe unit 101 in case of exchanging the optical probe unit 101. Further, the one-axis stage 232 also functions as an adjusting means for adjusting an offset. For example, even in a case in which the distal end of the optical probe unit 101 is not closely-attached to the surface of the biological tissue, it becomes possible, by changing the optical path length with the one-axis stage 232, to set it in a state of interfering from the surface position of the biological tissue.

Through mirrors 227, 229 and a lens 228, the reflected light is inputted as a reference light to the second single mode fiber 231. The reference light, whose optical path length is fine-adjusted by the variable mechanism 225 of the optical path length, is mixed with the reflected light from the first single mode fiber 230 side in the photo coupler unit 226 provided in the path of the second single mode fiber 231, and thus the reference light becomes an interference light, and is light-received by PD 219.

The light which is light-received by the PD 219 is photo-electrically converted and becomes an electrical signal. The signal is inputted to and amplified by an amplifier 220, and thereafter, is supplied to a demodulator 221. In the demodulator 221, a demodulation process for extracting only the signal component of the coherent light is carried out and the output thereof is inputted to an A/D converter 222.

In the A/D converter 222, digital data "coherent light data" of one line is produced by sampling the coherent light signal for 2048 points by 176 MHz. The sampling frequency is preferably set to 180 MHz because it is assumed that about 90% of the cycle (12.5 µsec) of the wavelength sweep is to be extracted as the digital data of 2048 points, in the case of setting the repeat frequency of the wavelength sweep to be 80 kHz, although the imaging apparatus disclosed here is not especially limited by this aspect.

The coherent light data per line unit produced in the A/D converter 222 is inputted to the signal processing unit 223. In this signal processing unit 223, the coherent light data are frequency-decomposed depending on an FFT (Fast Fourier Transform) and then, data is generated in the depth direction, and by coordinate-converting the data, a cross-sectional image is formed at each position of the blood vessel and it is outputted to an LCD monitor 113 at a predetermined frame rate.

The signal processing unit 223 is connected with an optical path length adjuster control unit 218. The signal processing unit 223 carries out the control of the position of the one-axis stage 232 through the optical path length adjuster control unit 218. Also, the signal processing unit 223 is connected with a motor control circuit 224 and stores the cross-sectional image in an internal memory by being synchronized with a video synchronous signal upon forming a cross-sectional image. In addition, the video synchronization signal of this motor control circuit 224 is transmitted to the rotary drive apparatus 204 and the rotary drive apparatus 204 outputs the drive signal in synchronization with the video synchronization signal. Further, a situation is created in which the signal processing unit 223 executes sampling of the interference light by the above-mentioned PD 219 or A/D converter 222.

Figure 4A:
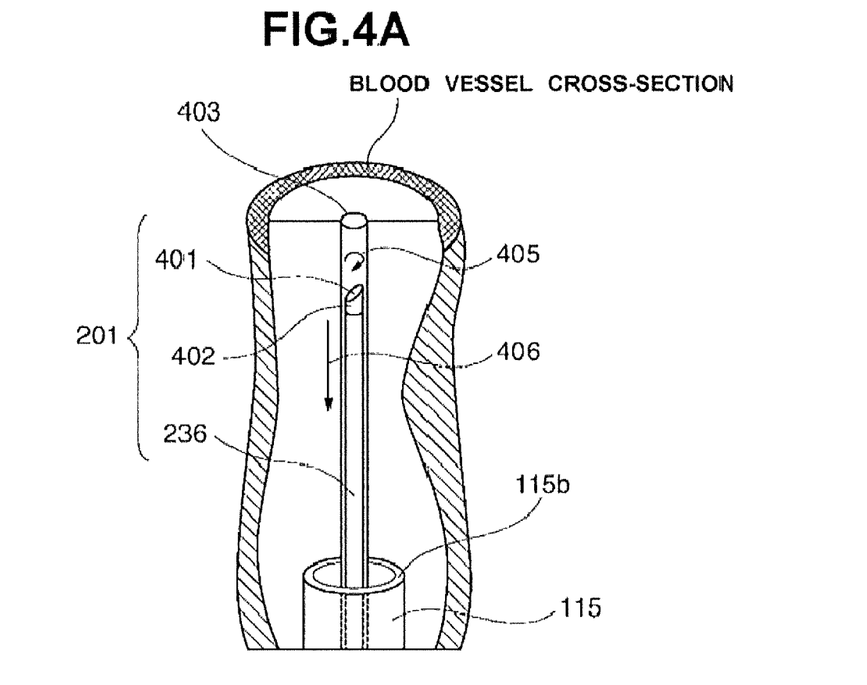
FIGS. 4A and 4B are cross-sectional views illustrating a rotation scanning and an axial movement of an optical probe unit inside a blood vessel, and illumination of a measurement light and taking-in of a reflected light.
Figure 4B:
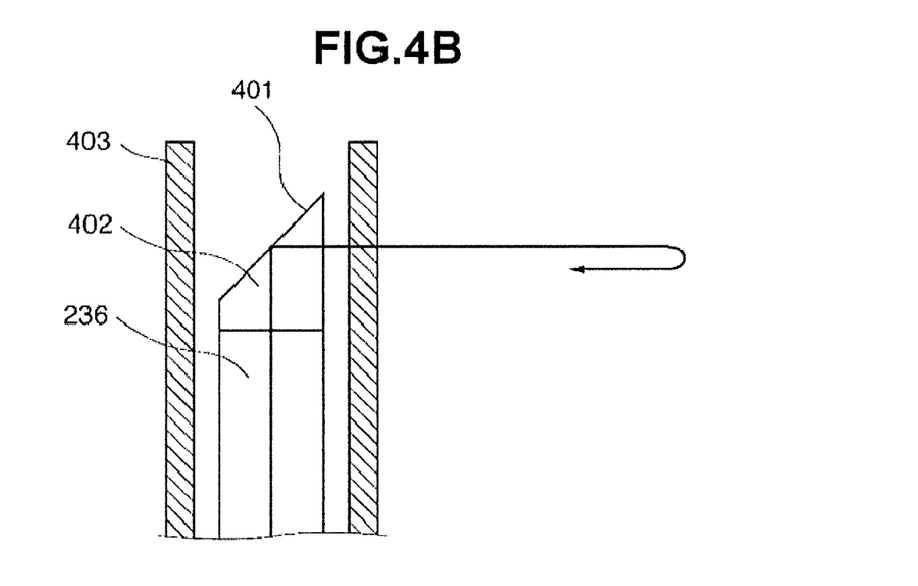

FIG. 4A is a view for explaining, by way of example, an aspect of the disclosure in which the imaging core 201 at the distal end of the optical probe unit 101 is inserted into the inside of a body lumen (inside of a blood vessel) and a radial scan is carried out. The catheter sheath 403 installed with an imaging core 201 comprising an optical fiber 236 including an optical mirror 401 and an optical lens 402 at the distal end thereof is inserted, for example, into a blood vessel lumen through the guiding catheter 115 (see FIG. 1). The rotary drive apparatus 204 rotates the imaging core 201 inside the catheter sheath 403 in a direction of arrow 405, and the linear drive apparatus 207 moves it in a direction of arrow 406 (pull-back process). At that time, as shown in FIG. 4B, the measurement light from the wavelength swept light source 208 is illuminated to the biological tissue (blood-vessel wall) by the optical mirror 401 by way of the optical fiber 236. The reflected light of the illuminated light is returned to the operation control apparatus 103 by the optical mirror 401 by way of the optical fiber 236.

Figure 5A:
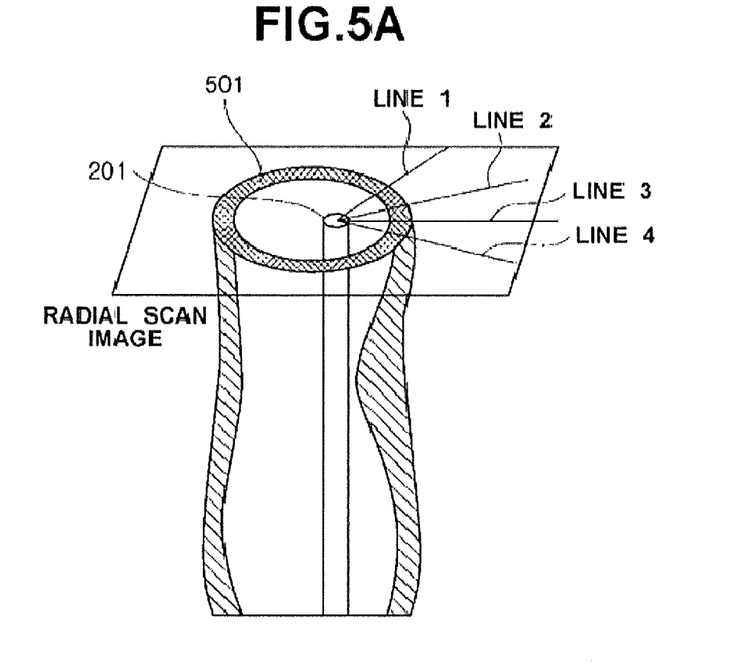
FIGS. 5A and 5B are schematic views illustrating an operation of an optical probe inside a blood vessel.
Figure 5B:
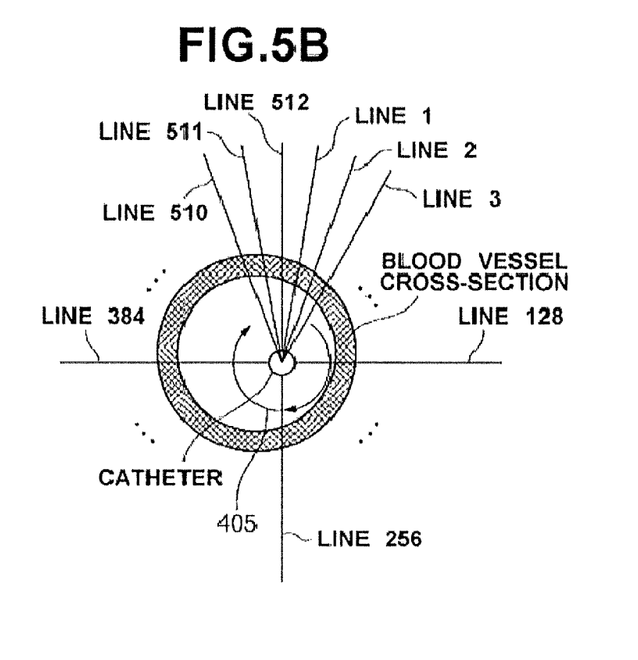

FIGS. 5A and 5B are schematic views for explaining an operation of the optical probe unit 101 when imaging a blood vessel tomographic image. FIGS. 5A and 5B are a perspective view and a cross-sectional view of the blood vessel, respectively, in a state in which the optical probe unit 101 is inserted. In FIG. 5A, a reference numeral 501 shows a blood vessel cross-section in which the optical probe unit 101 is inserted. As described above, the imaging core 201 of the optical probe unit 101 mounted with an optical lens 402 and an optical mirror at the distal end thereof rotates in a direction shown by reference numeral 405 by means of the radial scanning motor 205.

From the optical lens 402, the transmission and reception of measurement light is carried out at each rotary angle. Lines 1, 2, . . . , 512 show illumination directions of the measurement light at respective rotary angles. In this exemplified embodiment, while the imaging core 201 including the optical mirror 401 and the optical lens 402 rotates by 360 degrees at a predetermined position of a blood vessel cross-section 501, the transmission of the measurement light and the reception of the reflected light are carried out intermittently 512 times. The number of the transmission and reception times of the measurement light during the period when being rotated by 360 degrees is not limited by this number in particular, and it can be arbitrarily set. A scan (scanning) for repeating the transmission and reception of the signal while rotating the imaging core 201 in this manner is generally referred to as "radial scan (radial scanning, rotational scanning)". Also, such transmission of the measurement light and reception of the reflected light by the imaging core 201 are carried out while progressing inside the blood vessel in the arrow 406 direction (see FIG. 4A). The movement of the imaging core 201 in the direction of arrow 406 is carried out by driving the linear drive apparatus 207 in the scanner and pull-back unit 102 and by pulling a rotating fiber with a constant speed. Therefore, this operation is referred to as a pull-back operation.

In conformity with this pull-back operation, the flush operation for introducing the flush liquid into the target blood vessel lumen of the diagnosis, from the distal end of the guiding catheter 115, is carried out by operating the plunger of the flush liquid container 118. Thus, the blood vessel lumen obtains a state in which there exists no influence of the blood cell components of a red blood cell and the like in the inside of the blood and it is possible to obtain a highly accurate image.

Figure 3:
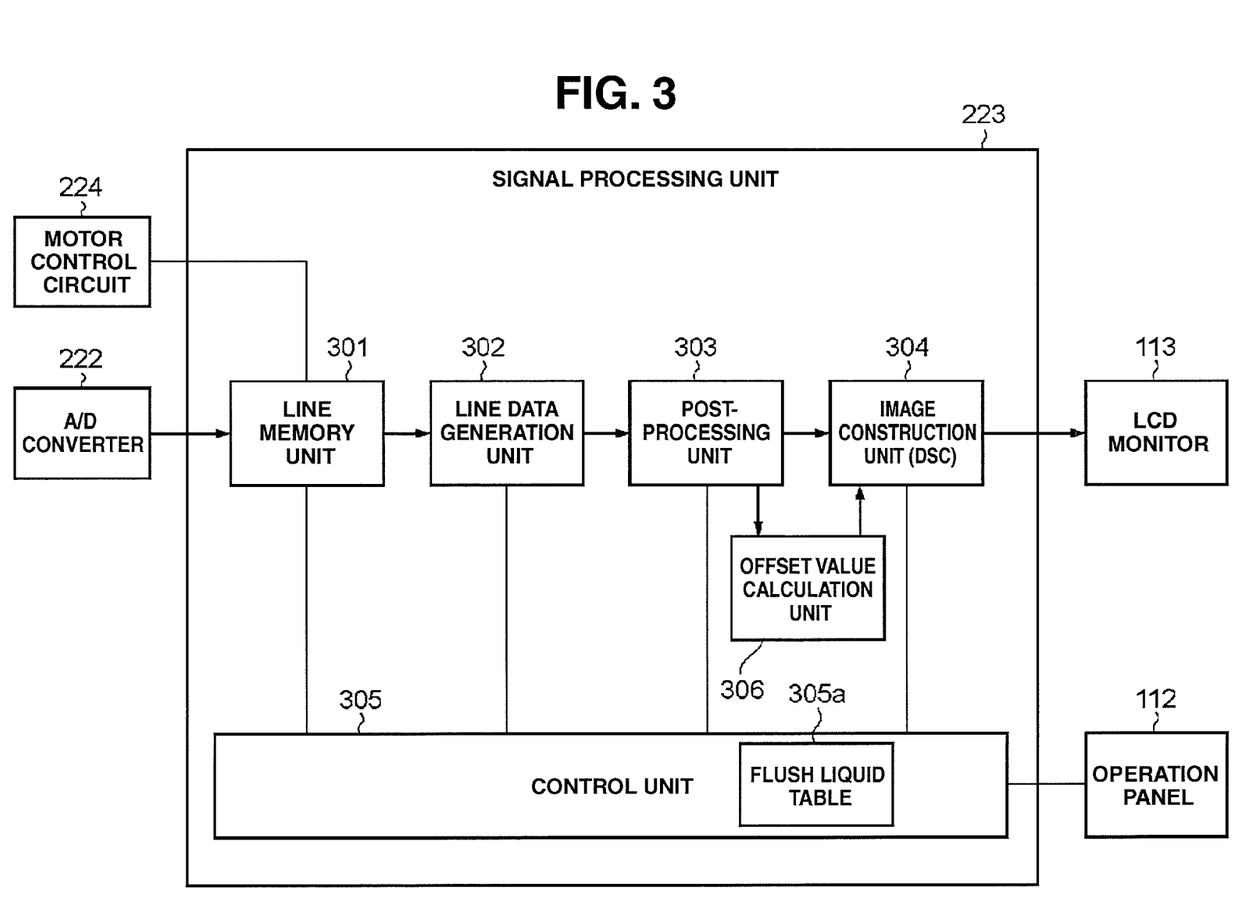
FIG. 3 is a functional block diagram showing a signal processing unit.

FIG. 3 shows the signal processing unit 223 in the exemplified embodiment. This signal processing unit 223 carries out a generation process of the tomographic image based on the electrical signal (signal from A/D converter 222) obtained from the interference light in the above-mentioned radial scan and pull-back operation in accordance with an instruction by the operator in the operation panel 112 and the operation unit 102a. The generation process will be explained as follows.

The signal processing unit 223 stores the interference light data for one line by the wavelength sweep from the A/D converter 222 into the line memory unit 301 sequentially. Then, based on an encoder signal of the motor, which is outputted from the motor control circuit 224, the signal is selected and grouped such that the number of lines per one rotation of the motor becomes 512 lines. More specifically, the interference data for every one line is outputted to the line data generation unit 302 for 512 data per one rotation of the motor.

The line data generation unit 302 generates line data by carrying out the FFT (Fast Fourie transform process) and concurrently, carries out a line addition-averaging process, a filter process, a logarithmic transform and the like, and outputs the obtained line data to a post-processing unit 303 in the succeeding stage.

In the post-processing unit 303, a contrast adjustment, an intensity adjustment, a gamma correction and the like are applied with respect to the line data received from the line data generation unit 302 and the process result thereof is outputted to an image construction unit 304. The image construction unit 304 converts the line data train of polar coordinates to a video signal and displays it on the LCD monitor 113 as a blood vessel cross-sectional image. The disclosure here is of one example in which the image is constructed out of 512 lines, but the disclosure is not to be limited by this number of lines.

An offset value calculation unit 306 is, as mentioned later, a unit for calculating an offset value based on the refractive index of a new flush liquid in order to correct the obtained calibration data or the tomographic image data in a case in which there is a change instruction of the flush liquid after the calibration operation.

A control unit 305 will control a series of the operations mentioned above. Also, in the control unit 305, there is a built-in memory for storing a flush liquid table 305a (details thereof will be mentioned later). Also, more detailed explanations relating to arithmetic contents until the above-mentioned blood vessel tomographic image is obtained and a display process thereof, which are carried out by the control unit 305 will be omitted.

Figure 6:
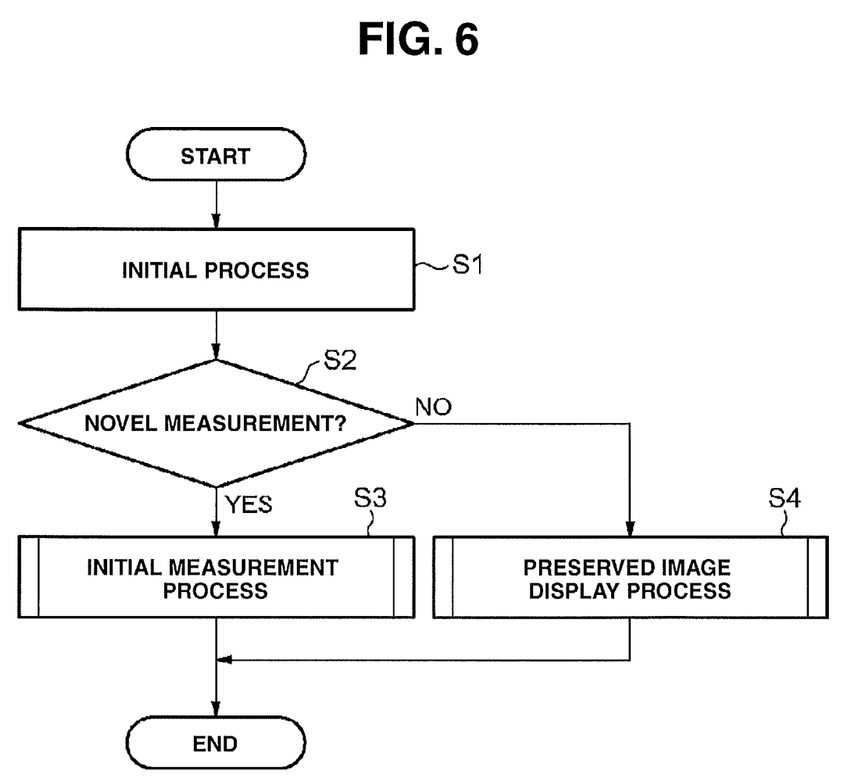
FIG. 6 is a flowchart showing a processing procedure of the imaging apparatus for diagnosis.

Explained below is a process of the signal processing unit 223 of the imaging apparatus for diagnosis in the exemplified embodiment in accordance with a flowchart in FIG. 6.

When a power supply of the imaging apparatus becomes ON, there is carried out, in step S1, an initialization process of various kinds of peripheral apparatuses which are connected to the apparatus. Subsequently, in step S2, a menu screen is displayed on the LCD monitor 113 and the operator is asked to select whether the mode is to be shifted to a novel measurement mode or whether the mode is to be shifted to a display mode of the preserved image measured in the past. This selection is to be carried out from the operation panel 112. Then, in accordance with the selected instruction, the flow will shift to a novel measurement mode (step S3) or will shift to a preserved image display process mode (step S4).

The process of the novel measurement mode process (step S3) will be explained next in accordance with a flowchart in FIG. 7. There is an assumption that the operator has already finished the work of inserting the distal end portion of the optical probe unit 101 as far as the blood vessel region which becomes the diagnosis target of the patient through the guiding catheter 115.

In order to obtain the tomographic image of the blood vessel over a predetermined distance along a blood vessel axis thereof, it is necessary to fill the inside of the blood vessel in the measurement range thereof with the flush liquid for excluding blood cell components (red blood cells and the like). However, there are several types of flush liquid and the refractive indexes thereof are different respectively. Consequently, first, there is carried out the selection of the flush liquid to be used.

The flush liquid table 305a inside of the control unit 305, which was explained previously, stores data having "Name and Refractive-Index" of the flush liquid as a pair items. Then, a name list of the flush liquids is displayed on the LCD monitor 113 in order to be selected by the operator and one is to be selected from those liquids through the operation panel 112 (step S101). It is customary for the name of the flush liquid to include a numeric character which expresses the percentage of content of the contrast agent (or percentage of content of the physiological salt solution).

Thereafter, a calibration process is executed on the assumption of the use of the selected flush liquid (step S102). Hereinafter, this calibration process will be explained in more detail.

The light speed propagating in the inside of a medium depends on the refractive index which that medium possesses. More specifically, there occurs a phenomenon that the light speed changes corresponding to the type of the flush liquid, so that it becomes necessary, first, to employ a calibration process for arranging the most suitable scan condition for the flush liquid which is scheduled to be used.

Consequently, the control unit 305 instructs the radial scanning motor 205 inside of the scanner and pull-back unit 102 to be driven and rotates the optical mirror 401 inside the optical probe unit 101. Then, the image of the boundary surface between the catheter sheath 403 and the blood is displayed on the LCD monitor 113. As explained previously, although the catheter sheath 403 is transparent, some amount of light reflection is obtained at the boundary surface thereof.

Also, on the LCD monitor 113, a target circle is displayed for carrying out the calibration. Then, by carrying out an instruction for scaling up or scaling down the scale of a circle on the boundary surface of the catheter sheath 403, which was obtained by the actual measurement, from the operation panel 112, the two circles, i.e., the target circle and the actually measured circle, are adjusted so as to overlap each other. In other words, the adjusting work is carried out by using a user interface defined by the operation panel 112 and the LCD monitor 113. For the process of the control unit 305 at that time, there is calculated an adjustment value by using a value expressing the degree of scaling-up and scaling-down which the operator instructed and the refractive index of the flush liquid selected previously, and there is carried out a process for adjusting the optical path length of the reference light by controlling the variable mechanism 225 of the optical path length based on the adjustment value. The LCD monitor 113, for displaying the circles of the target circle and the actually measured circle, and the operation panel 112 function as an adjustment value setting unit. When an adjustment of the optical path length is to be carried out on the user interface, the circle on the boundary surface of the catheter sheath 403 which was obtained by actual measurement, is scaled up or scaled down and it is thus possible for the operator to carry out this calibration merely by carrying out the overlapping procedure of the two circles.

Now, when the overlapping of the two circles is completed in accordance with the above description, the optical path length of the measurement light and the optical path length of the reference light, in the case of having been measured by using the set flush liquid, coincide with each other, and thus the preparation is ready for carrying out the flush operation and the pull-back operation.

It is assumed that an instruction for changing the flush liquid to be utilized is inputted for some reason (step S103). A lot of cases fall into this case in which the flush liquid (refractive index) selected before the calibration operation was erroneous. In this case, it is acceptable if the correct flush liquid (refractive index) is newly selected and the procedure relating to the above-mentioned calibration operation is carried out. However, the process of making the above-mentioned two circles conform to each other is bothersome and it increases the burden on the operator. Consequently, in this exemplified embodiment, in a case in which there was a change instruction of the flush liquid, the line data from when the calibration operation was previously carried out in accordance with the refractive index $n_{false}$ is utilized and an offset value is calculated in the offset value calculation unit 306 based on the refractive index $n_{true}$ of the correct flush liquid, and the calibration is re-executed automatically by the calculation (process for adjusting optical path length of reference light is also automated). This automation process is to be carried out in step S104.

Figure 9:
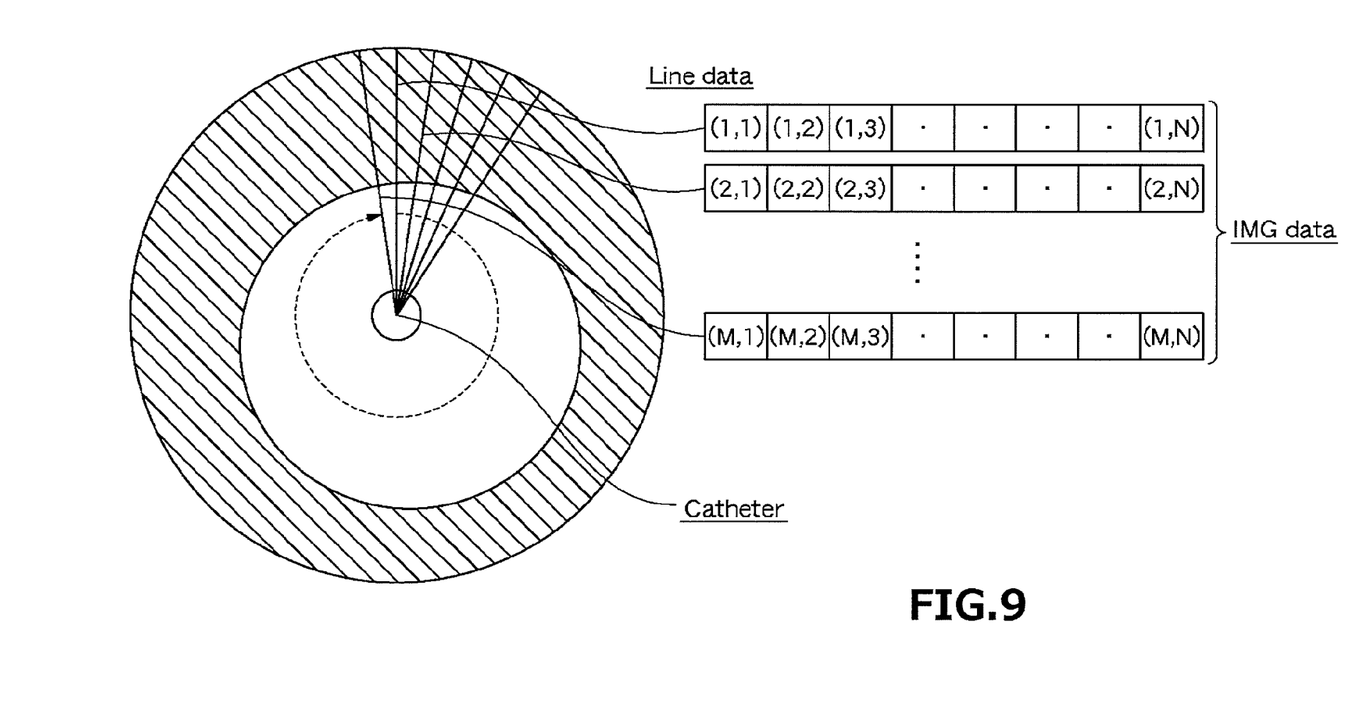
FIG. 9 is a diagram showing a relation between respective lines and line data of original data of a tomographic image in a radial scan.

FIG. 9 illustrates a principle of constructing the tomographic image. In the exemplified embodiment, the intensity data of the light of the interference light for M lines (M=512 in the exemplified embodiment) are obtained by the wavelength sweep during one rotation of the optical mirror 401 and based on those signals, the line data are calculated for M lines extending on the radial lines centering around the position of the optical mirror 401. The respective line data are, as shown FIG. 9, pixel data on the radial lines extending from a scan center position (position of optical mirror 401), so that naturally, the farther the lines are apart from the scan center position, the farther apart the distance between the neighboring two lines becomes apart, and the empty space therebetween is spreading. On the other hand, the image to be displayed on the display apparatus is in a state of being filled with the pixels both horizontally and vertically, so that it is necessary to generate the pixels between the above-mentioned lines by interpolation.

Figure 10:
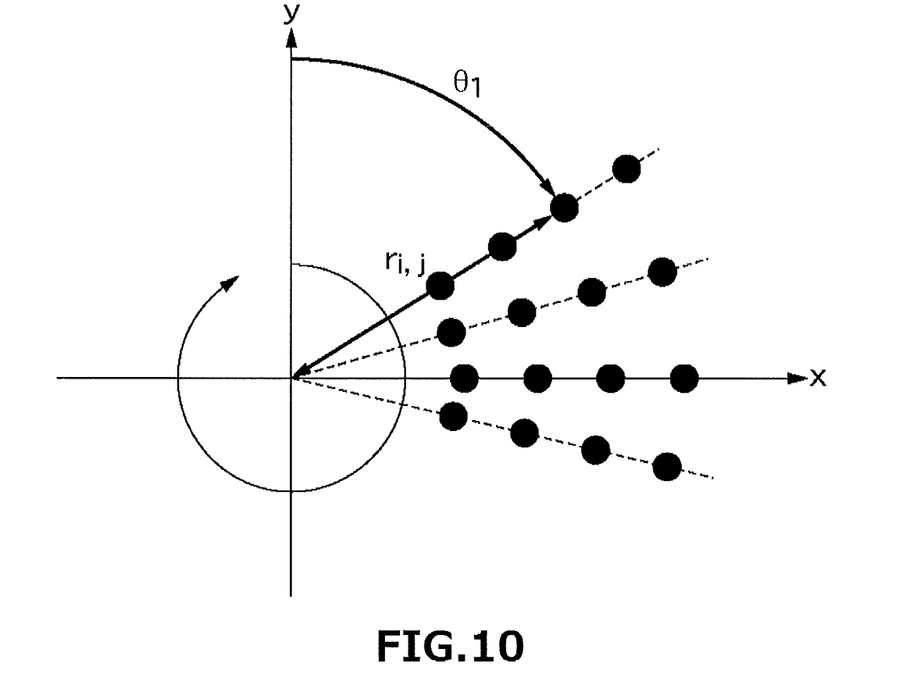
FIG. 10 is a diagram showing that the line data are expressed by polar coordinates.
Figure 11:
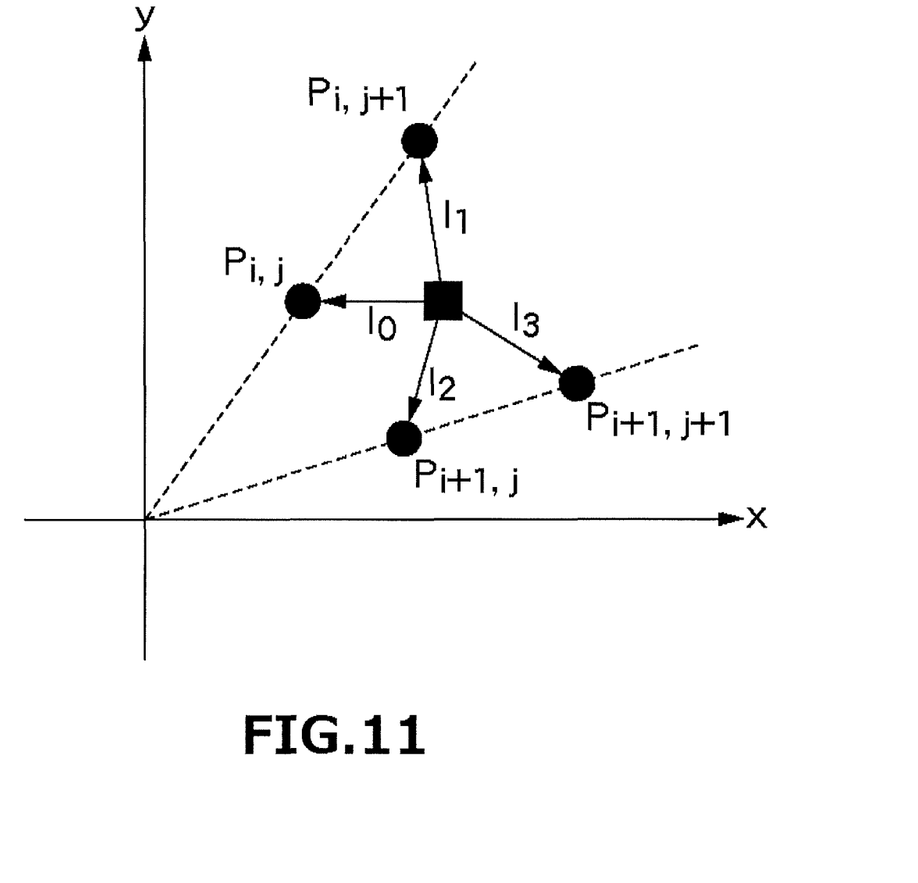
FIG. 11 is a diagram for illustrating an algorithm of calculating an interpolation pixel value from a pixel value of polar coordinates by linear interpolation.

Consequently, the tomographic image is constructed by calculating the pixels in a two-dimensional empty space, for example, by using four-point linear interpolation (see FIG. 10, FIG. 11).

$$xij = rij \cdot \sin fi$$

$$yij = rij \cdot \cos fi \quad (1)$$

Here, (xij, yij) belong to the coordinate system in which the center of the tomographic screen is made to be an original point and a value sampled at the j-th in the i-th line data is expressed, and (rij, θij) expresses the coordinate of the straight-ahead direction and the circumferential direction of that beam.

It is assumed that a calibration was carried out previously by selecting an incorrect flush liquid, in which the optical path length difference between the reference light and the measurement light was made to be zero. In this state, if it is assumed that the correct flush liquid having a refractive index different from the refractive index selected previously is newly selected and that all other parameters are employed while not being changed, there is created a situation in which the target circle and the actually measured circle are displayed as being deviated each other. For example, there occurs a situation in which the circle having a radius R which was actually previously measured becomes a circle having a radius R'.

This phenomenon is synonymous with a phenomenon in which "rij" in the equation (1) is moving linearly with respect to a position at which the optical path length difference is zero. In other words, in the case of changing the refractive index to the correct one, it is acceptable if the image is re-constructed by adding an offset value (Offset) as shown in the following equation (2).

$$x_{i,j} = (r_{ij} + \text{Offset}) \sin \theta_i$$

$$y_{i,j} = (r_{ij} + \text{Offset}) \cos \theta_i \quad (2)$$

It is known that the maximum depth of a sample, which can obtain an interference signal, is inversely proportion to an refractive index as shown in the following equation (3).

$$z = \lambda 2/(4n\delta\lambda) \quad (3)$$

where a symbol n denotes refractive index, a symbol $\lambda 1$ denotes center wavelength of a light source to be used and a symbol $\delta\lambda$ denotes swept wavelength width.

In other words, in a case in which the refractive index changes, the maximum depth which the line data shown by FIG. 9 possesses is different depending on equation (3) and therefore, as a result thereof, the depth information which one line data possesses is inversely proportion to the refractive index. That is to say, "rij" of the equation (1) is also inversely proportion to the refractive index as shown in the following equation (4). Note that symbol N expresses the number of data which constitutes the line.

$$r_{ij} = (j/N) \times z = (j/N) \times \lambda 2/(4n\delta\lambda) \quad (4)$$

In this exemplified embodiment, by utilizing data for which the calibration was carried out on the basis of the refractive index of the incorrect flush liquid, the control unit 305 controls the variable mechanism 225 of the optical path length and corrects the optical path length, with respect to the optical path length of the reference light which was adjusted at that time, such that it becomes an optical path length added with a value as much as the above-mentioned Offset amount, which becomes comparable to the refractive index of the correct flush liquid. This "Offset" is calculated in the following manner.

When assuming that the refractive index of the actually used flush liquid is made to be $n_{true}$ and the refractive index of the flush liquid selected by mistake is made to be $n_{false}$, the following relation is satisfied between $r_{ij\_true}$ which is the coordinate in the straight-ahead direction of the original beam and the coordinate $r_{ij\_false}$ which is calculated by mistake.

$$r_{ij\_true} = \frac{j}{N} \times \frac{\lambda^2}{4n_{true}\delta\lambda} \quad \text{Equation (5)}$$

$$= \frac{j}{N} \times \frac{\lambda^2}{4n_{false}\delta\lambda} \times \frac{n_{false}}{n_{true}}$$

$$= \frac{n_{false}}{n_{true}} \times r_{ij\_false}$$

Since the Offset value is a difference between the coordinate of the $n_{true}$ and the coordinate of the $n_{false}$) the offset value is expressed by equation 6 as follows.

$$\text{Offset} = r_{ij\_true} - r_{false} = \frac{j}{N} \times \left(1 - \frac{n_{true}}{n_{false}}\right) \times \frac{\lambda^2}{4n_{true}\delta\lambda} \quad \text{Equation (6)}$$

Figure 7:
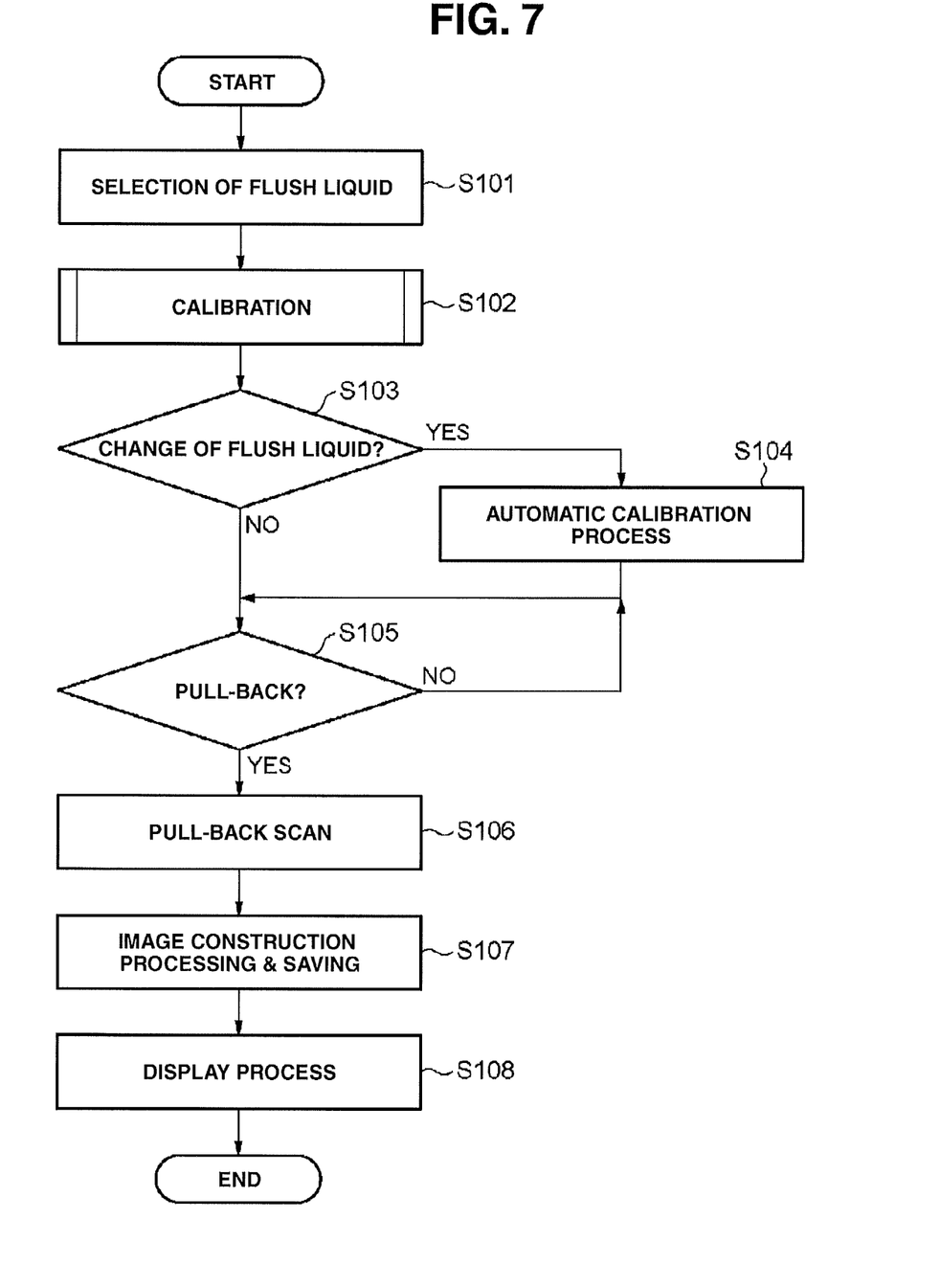
FIG. 7 is a flowchart showing details of a novel measurement process in FIG. 6.

The foregoing is the automatic re-calibration process in step S104 of FIG. 7 in the exemplified embodiment.

When the flush liquid actually used is set as explained above and the calibration is completed, preparation for the pull-back process is completed. Consequently, the operator operates the plunger of the flush liquid container 118 and causes the flush liquid to flow out to the measurement region. Thereafter, when detecting the operation of a pull-back switch (not shown) which is provided at the operation unit 102a of the scanner and pull-back unit 102 (step S105), the control unit 305 drives the linear drive apparatus 207 and, as shown in FIG. 4A, the pull-back process for moving the optical mirror 401 during the rotation in the arrow 406 direction is carried out (S106). During this pull-back process, data relating to the interference light are received sequentially from the A/D converter 222 and during the movement of the optical mirror 401, and the construction process of the tomographic image is carried out at the respective positions of the blood vessel (step S107). All the tomographic images obtained at that time and also the interference light data (IMG_DATA in FIG. 9), which became the source for obtaining the tomographic images thereof, are stored in a data storage unit such as a hard disk or the like which is not shown in the drawing. In addition to the data shown in FIG. 9, the type of the selected flush liquid (or the refractive index) is also stored in this file.

When the pull-back process finishes, the constructed tomographic image is displayed on the LCD monitor 113 (step S108), with an actual-size scale attached thereto, and this process finishes.

Figure 8:
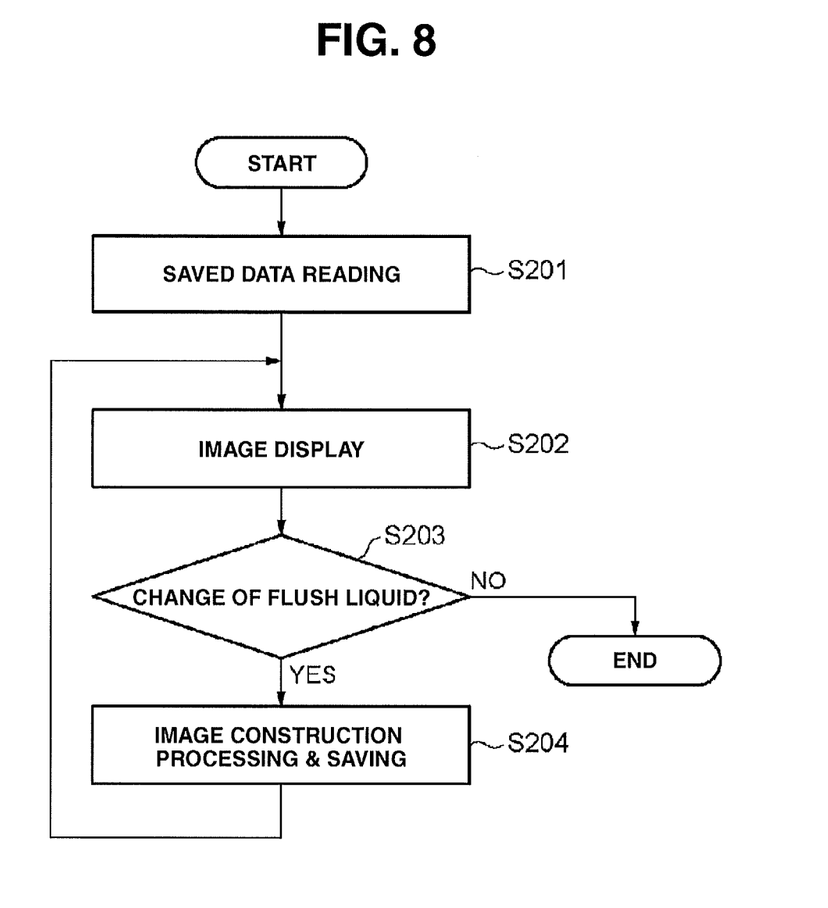
FIG. 8 is a flowchart showing details of a preserved image display process in FIG. 6.

Next, a preserved image display process at step S4 in FIG. 6 will be explained in accordance with the flowchart in FIG. 8. This process for the exemplified embodiment is not restricted to only the confirmation of the tomographic images scanned in the past, but also applies to a case in which the pull-back process and the data storing process have been carried out while having an erroneous selection of the flush liquid.

First, the control unit 305 finds a predetermined file in the data files saved in a hard disk which is not shown in the drawing and image data of that file are read (step S201). It is assumed that the file name includes key information such as a patient name, scan date and the like, such that a search can be carried out with reference thereto. Alternatively, it is possible to search a desired file by preparing an exclusive data base and by searching the key information.

Based on the read data, the tomographic image and the name of the selected flush liquid are displayed on the LCD monitor 113 (step S202).

Here, in a case in which the operator notices an error by looking at the name of the flush liquid displayed, a change instruction is given from the operation panel 112. Upon receipt of this instruction, the control unit 305 displays a list of selectable flush liquids with reference to the flush liquid table 305a, and allows selection to be carried out (step S203).

When a re-setting of the flush liquid is instructed, the refractive index $n_{true}$ of the re-set flush liquid thereof is determined. On the other hand, since the information of the incorrect flush liquid had been stored in the selected file, it is also possible to obtain the refractive index $n_{false}$ thereof. Furthermore, data during the movement of the optical mirror 401 (see FIG. 9) are stored in the file. Therefore, by using these data, an offset value (Offset) is calculated in accordance with equation (6) indicated above and the re-construction process of the tomographic image is executed based on the (refractive index $n_{true}$ of) the flush liquid which is newly set in accordance with the equation (2) (step S204). At that time, the correct refractive index $n_{true}$ is newly recorded. However, there is no change with respect to data and refractive index $n_{false}$ during the movement of the optical mirror 401. When the re-construction process is finished in this manner, the process returns to step S202, the data of that tomographic image are read out, and the display thereof is carried out.

According to the above aspects, when an operator of the optical coherent tomographic diagnostic apparatus is aware that there was an error in the selection of the flush liquid after the calibration operation or after the termination of the imaging operation, the apparatus can semi-automatically carry out correction of calibration or image data, i.e., the work relating to re-calibration and re-imaging work, without carrying out the work relating to the calibration again or without carrying out the pull-back operation again. The correction is based on the new refractive index newly set by the operator and the result data of the already carried out calibration or the image data after the measurement.

As explained above, according to this exemplified embodiment, in the optical coherent tomographic diagnostic apparatus, during such procedures as the setting of the flush liquid, the calibration operation, or the pull-back operation, which are carried out by the operator, it is possible to eliminate the necessity of returning to the calibration operation in a case in which a change in the flush liquid was carried out after noticing an error in the type of set-up flush liquid after the calibration. More specifically, by processing the re-calibration operation thereof automatically, it becomes possible to avoid an increase in the surgical-operation time period or in the number of surgical-operations and it becomes possible to also make the procedures performed by the operator more simple and convenient, while also decreasing the stress exerted on the patient.

An optical coherent tomographic image forming apparatus according to one embodiment, as disclosed here by way of example, which divides a light outputted from a light source into a measurement light and a reference light by using a photo coupler thus includes: a flush unit for discharging flush liquid; a refractive index setting unit for selecting a refractive index of the flush liquid within a plurality of refractive indexes; an adjustment value setting unit for setting the adjustment value for adjusting the optical path length of the reference light; a calibration unit composed of an optical path length adjuster; a pull-back unit for discharging the flush liquid in the body lumen; an image construction unit for constructing the cross-sectional image based on the sampled interference light data; and an offset value calculation unit for calculating an offset value of the optical path length of the reference light based on the changed refractive index.

Having described preferred embodiments with reference to the accompanying drawings, it is to be understood that the invention is not limited by those precise embodiments and that various changes and modifications could be effected therein by one skilled in the art without departing from the spirit or scope of the invention as defined in the appended claims.

What is claimed is:

1. An optical coherent tomographic image forming apparatus comprising:
a light source;
a light guide configured to guide a light outputted from the light source and divide the light into a measurement light and a reference light, the light guide including a measurement optical path and a reference optical path;
an optical probe having a distal end and a proximal end, the distal end being configured for insertion into a body lumen;
a flush unit including a flush liquid container and a flush liquid discharger, the flush unit configured to discharge a flush liquid into the body lumen;
a refractive index setting unit configured to set a refractive index of the flush liquid;
an adjustment value setting unit configured to set an adjustment value for adjusting a difference between a length of the measurement optical path and a length of the reference optical path, the adjustment value being determined using the refractive index of the flush liquid;
a calibration unit comprising an optical path length adjuster for adjusting the length of the reference optical path or the length of the measurement optical path based on the adjustment value;
an image construction unit configured to construct a cross-sectional image based on a light intensity of an interference light that is obtained from a reflected light obtained by emanating the measurement light from the optical probe toward a biological tissue defining the body lumen while the flush liquid subsists in the body lumen; and
an offset value calculation unit for calculating an offset value of the length of the reference optical path based on a changed refractive index when the refractive index of the flush liquid is changed by the refractive index setting unit after calibration is executed by the calibration unit.

2. The optical coherent tomographic image forming apparatus according to claim 1, further comprising a data storage unit configured to store data relating to the cross-sectional image, wherein after calibration is executed by the calibration unit and when the refractive index of the flush liquid is changed by the refractive index setting unit before data is stored, the optical path length adjuster adjusts the optical path length of the reference light automatically based on the offset value calculated by the offset value calculation unit.

3. The optical coherent tomographic image forming apparatus according to claim 1, further comprising a data storage unit configured to store data relating to the cross-sectional image, wherein after data is stored by the data storage unit and when the refractive index of the flush liquid is changed by the refractive index setting unit, the image construction unit corrects the data and reconstructs a corrected cross-sectional image based on the offset value calculated by the offset value calculation unit.

4. The optical coherent tomographic image forming apparatus according to claim 1, wherein the refractive index setting unit is configured to select a numeral indicating the percentage of content of a contrast agent in the flush liquid.

5. The optical coherent tomographic image forming apparatus according to claim 1, wherein the refractive index setting unit is configured to select a numeral indicating the percentage of content of a physiological salt solution in the flush liquid.

6. The optical coherent tomographic image forming apparatus according to claim 1, wherein the light source is a wavelength swept light source.

7. The optical coherent tomographic image forming apparatus according to claim 1, wherein the changed refractive index is based on a refractive index of a changed flush liquid.

8. The optical coherent tomographic image forming apparatus according to claim 1, wherein the calibration unit further comprises a LCD monitor for displaying a target circle and a circle obtained by actual measurement, the adjustment value setting unit scaling up or scaling down the circle obtained by actual measurement so as to overlap with the target circle.

9. The optical coherent tomographic image forming apparatus according to claim 8, wherein, when the circle obtained by actual measurement overlaps with the target circle, a length of the measurement optical path and a length of the reference optical path coinciding with each other.

10. A control method for an optical coherent tomographic image forming apparatus which divides a light outputted from a light source into a measurement light and a reference light by using a photo coupler and which generates a cross-sectional image of a biological tissue of a test object based on light intensity of an interference light that is obtained from a reflected light obtained by emanating the measurement light from a rotatable optical mirror provided at a position in the vicinity of a distal end of an optical probe unit insertable into a body lumen of the test object toward the biological tissue and away from the reference light, the method comprising:

a selection step for selecting a refractive index for one of a plurality of flush liquids which can be discharged from the distal end of the probe into the blood vessel, the refractive index being set corresponding to the type of flush liquid selected in response to instruction of an operator;

a calibration step including setting an adjustment value for adjusting the optical path length of the reference light under the selected refractive index in response to an operation of the operator in order to make the optical path length of the measurement light and the optical path length of the reference light coincide with each other, and adjusting the optical path length of the reference light based on the adjustment value; and an offset value calculation step for calculating an offset value of the optical path length of the reference light based on a changed refractive index when the refractive index of the flush liquid is changed after the calibration process.

11. A method of controlling an optical coherent tomographic image forming apparatus comprising a light source; a light guide configured to guide a light outputted from the light source and divide the light into a measurement light and a reference light, the light guide including a measurement optical path and a reference optical path; and an optical probe having a distal end and a proximal end, the distal end being configured for insertion into a body lumen; the method comprising:

selecting a set flush liquid intended to be discharged into the body lumen;

setting a refractive index based upon the selected set flush liquid;

setting an adjustment value for adjusting a difference between a length of the measurement optical path and a length of the reference optical path, the adjustment value being determined using the refractive index of the selected flush liquid;

calibrating the optical coherent tomographic image forming apparatus by adjusting the length of the reference optical path or the length of the measurement optical path based on the adjustment value;

constructing a cross-sectional image based on a light intensity of an interference light that is obtained from a reflected light obtained by emanating the measurement light from the optical probe toward a biological tissue defining the body lumen; and calculating an offset value of the length of the reference optical path based on a changed refractive index when the refractive index of the flush liquid is changed after calibrating the optical coherent tomographic image forming apparatus.

12. The method according to claim 11, further comprising discharging an actual flush liquid into the body lumen, the actual flush liquid being different from the set flush liquid.

13. The method according to claim 12, further comprising setting the changed refractive index based on the actual flush liquid, the changed refractive index being different from the refractive index of the selected set flush liquid.

14. The method according to claim 13, further comprising adjusting the optical path length of the reference light automatically based on the calculated offset value.

15. The method according to claim 14, wherein after calibrating the optical coherent tomographic image forming apparatus, setting the changed refractive index based on the actual flush liquid, and adjusting the optical path length of the reference light automatically based on the calculated offset value, the method further comprising:

storing data relating to the cross-sectional image.

16. The method according to claim 14, further comprising storing data relating to the cross-sectional image.

17. The method according to claim 16, wherein after storing data relating to the cross-sectional image and setting the changed refractive index based on the actual flush liquid, the method further comprising:

reconstructing a corrected cross-sectional image based on the calculated offset value.

18. In an optical coherent tomographic image forming apparatus comprising a light source; a light guide configured to guide a light outputted from the light source and divide the light into a measurement light and a reference light, the light guide including a measurement optical path and a reference optical path; an optical probe having a distal end and a proximal end, the distal end being configured for insertion into a body lumen; a refractive index setting unit configured to set a refractive index of a flush liquid; means for calibrating the optical coherent tomographic image forming apparatus based upon a set flush liquid; and an image construction unit configured to construct a cross-sectional image; the improvement comprising an offset value calculation unit for calculating an offset value of the length of the reference optical path based upon a changed refractive index;

wherein an actual flush liquid discharged into the body lumen is different from the set flush liquid such that the refractive index setting unit sets the changed refractive index after calibrating the optical coherent tomographic image forming apparatus.

19. The improvement according to claim 18, further comprising means for automatically recalibrating the optical coherent tomographic image forming apparatus based upon the offset value.

20. The improvement according to claim 18, wherein the image construction unit is configured to reconstruct the cross-sectional image based upon the offset value.

21. The improvement according to claim 18, wherein the offset value is calculated according to the following equation:

$$\text{Offset} = r_{ij\_true} - r_{false} = \frac{j}{N} \times \left(1 - \frac{n_{true}}{n_{false}}\right) \times \frac{\lambda^2}{4n_{true}\delta\lambda}.$$

* * * * *